US012544275B2

(12) United States Patent
Hoffman et al.

(10) Patent No.: US 12,544,275 B2
(45) Date of Patent: Feb. 10, 2026

(54) COMPRESSION WRAP WITH A STARTING PORTION FORMED AS A TONGUE

(71) Applicant: SIGVARIS AG, St. Gallen (CH)

(72) Inventors: Keith Hoffman, Hamilton, MI (US); Laure Kuipers, Holland, MI (US)

(73) Assignee: SIGVARIS AG, St. Gallen (CH)

( * ) Notice: Subject to any disclaimer, the term of this patent is extended or adjusted under 35 U.S.C. 154(b) by 110 days.

(21) Appl. No.: 18/600,162

(22) Filed: Mar. 8, 2024

(65) Prior Publication Data

US 2025/0281335 A1 Sep. 11, 2025

(51) Int. Cl.
*A61F 13/00* (2024.01)
*A61F 13/02* (2006.01)

(52) U.S. Cl.
CPC ................................ *A61F 13/0273* (2013.01); *A61F 2013/00591* (2013.01); *A61F 2013/00795* (2013.01)

(58) Field of Classification Search
CPC .... A61F 2013/00591; A61F 2013/0153; A61F 2013/8497; A61F 13/085; A61F 13/0153
USPC .............................................................. 602/75
See application file for complete search history.

(56) References Cited

U.S. PATENT DOCUMENTS 2,687,723 A * 8/1954 Stern ..................... A61F 13/085 602/75
9,125,727 B2 9/2015 Dallafior
2016/0120176 A1 5/2016 Sanghi et al.
2017/0020707 A1 1/2017 Duport

FOREIGN PATENT DOCUMENTS

CA 2603553 A1 10/2006
DE 102015226368 A1 6/2017
EP 2057974 A1 5/2009
EP 2275062 B1 7/2016
EP 3393413 A1 10/2018
WO WO-9402090 A1 * 2/1994 ......... A61F 13/0273
WO 2023037290 A1 3/2023

* cited by examiner

*Primary Examiner* — Kim M Lewis
(74) *Attorney, Agent, or Firm* — BakerHostetler

(57) ABSTRACT

A compression bandage adapted to be wrapped around a body part in a helicoidal manner. The compression bandage has a length (L) and a width (W) and the length (L) is several times greater than the width (W). The compression bandage includes a starting portion (1) and a central portion (2) adjacent to the starting portion (1). The starting portion (1) and the central portion (2) include a first part (4) and a second part (5). The first part (4) has a first thickness (T1) and a first width (W1) and the second part (5) has a second thickness (T2) and a second width (W2). The starting portion (1) includes an extension (6) of the first part (4) protruding past the end of the second part (5).

21 Claims, 3 Drawing Sheets

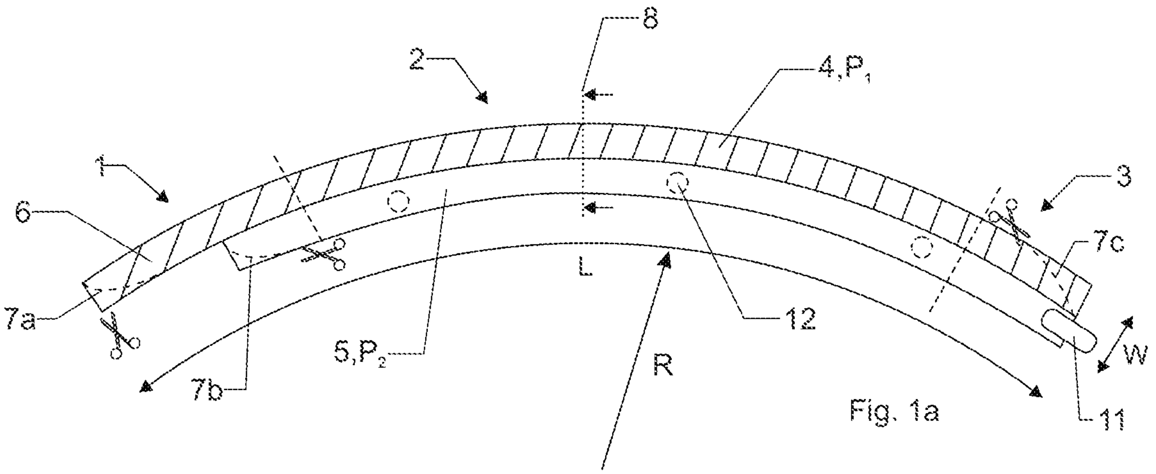
Fig. 1a
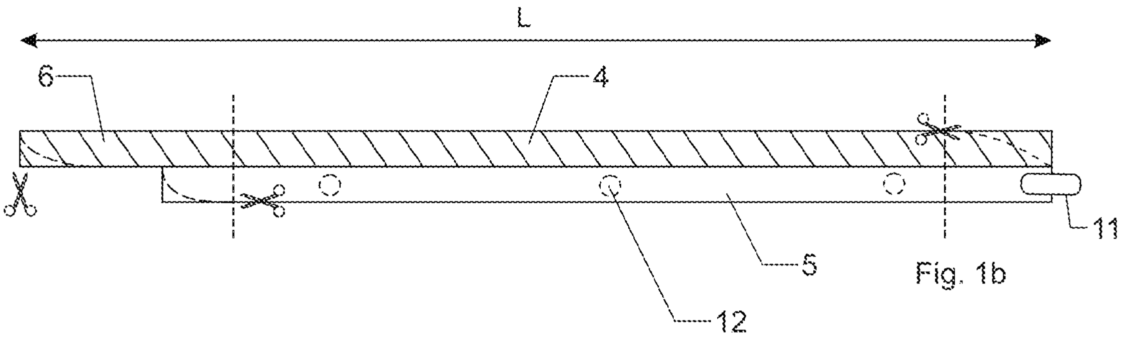
Fig. 1b
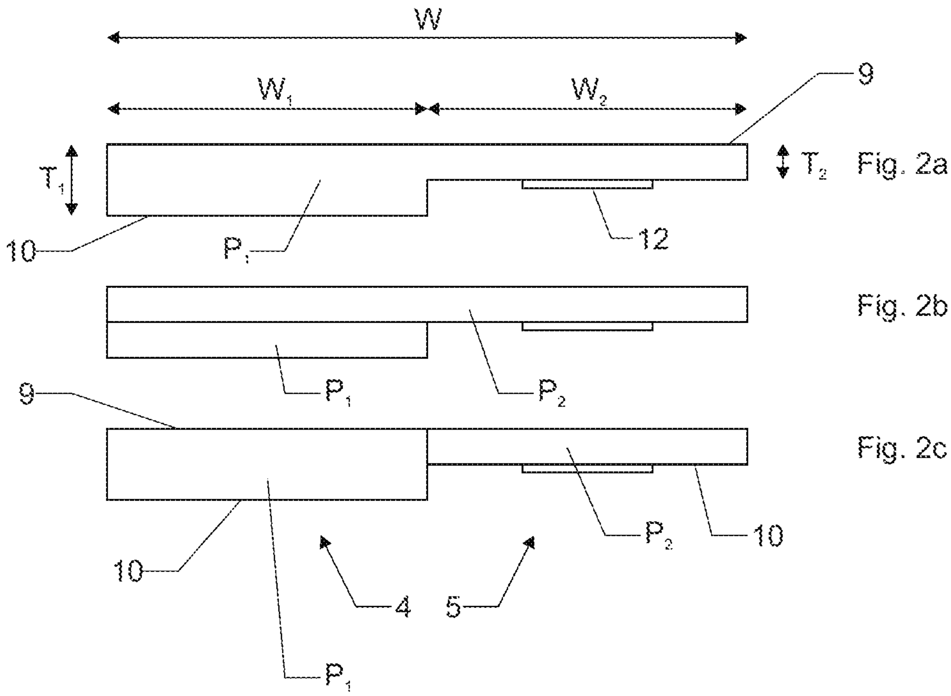
Fig. 2a
Fig. 2b
Fig. 2c

COMPRESSION WRAP WITH A STARTING PORTION FORMED AS A TONGUE

TECHNICAL FIELD

The invention relates to a compression bandage adapted to be wrapped around a body part in a helicoidal manner. The compression bandage has a length and a width and the length is several times greater than the width. The compression bandage comprises a starting portion and a central portion, wherein the central portion is adjacent to the starting portion. The starting portion and the central portion comprise a first part and a second part, both ex-tending over the entire length of the central portion. The first part extends across a part of the width of the compression bandage and the second part extends across a part of the remaining width of the compression bandage. The first part has a first thickness and a first width and the second part has a second thickness and a second width. At any point along its length, in the starting portion and in the central portion, the second width is at least half the first width and the first thickness is greater than the second thickness.

BACKGROUND ART

Multi-layer bandaging is the gold standard of care for lymphedema and other forms of edema. Multi-layer bandaging is typically applied in a clinical setting, with a trained therapist first wrapping the body part with a layer of cushioning (typically foam or non-woven cushioning). The cushioning acts to protect fragile skin, bridge small crevices or irregularities on the surface of the body part and acts to provide even pressure on the skin when the multi-layer bandaging is applied. The therapist then wraps the body part with a short stretch bandage to provide the desired level of compression. The bandage is typically overlapped by approximately 50% so that two layers of bandaging are uniformly applied.

While the multi-layer bandaging process described above is highly effective, it consumes a lot of the therapist's time, limiting the number of patients they can see in a day. In many areas, the availability of trained therapists is limited, so many patients are not able to secure the treatment they need.

Another disadvantage of this solution is that because the treatment is so effective, the bandages may loosen quickly after application as the body part reduces in size. As a result, the dosage of compression applied is greatly reduced, or the bandages may completely fall off and provide no therapy at all. Since the application of the bandaging is complex and best performed by a trained therapist, the patient may simply remove the bandages until their next appointment, or misapply them and receive inadequate or improper treatment. In some countries, such as the US, patients typically receive treatment only twice a week, so proper treatment is lacking for significant periods of time.

Another disadvantage of multi-layer bandaging is that costs can be high, especially considering that the cushioning materials may be single use or have limited life and must be replaced frequently.

DISCLOSURE OF THE INVENTION

The problem to be solved by the present invention is to provide an alternative to the traditional multi-layer bandaging which can more easily be applied in greatly reduced time by clinicians or therapists and can be applied and re-applied by the patient or home care providers.

This problem is solved by a compression wrap in the shape of a bandage according to the independent claim. According to this, the compression bandage is adapted to be wrapped around a body part in a helicoidal manner. The compression bandage comprises a length and a width and the length is several times greater than the width. The compression bandage comprises a starting portion and a central portion, wherein the central portion is adjacent to the starting portion. The starting portion and the central portion comprise a first part and a second part, both extending over the entire length of the central portion. The first part extends across a part of the width of the compression bandage and the second part extends across a part of the remaining width of the compression bandage. The first part has a first thickness and a first width and the second part has a second thickness and a second width. At any point along its length, in the starting portion and in the central portion, the second width is at least half the first width and the first thickness is greater than the second thickness. The starting portion comprises an extension of the first part protruding past the end of the second part.

When wrapping the compression bandage around the body part, the first part acts as a first cushioning layer over the body part. The bandage is wrapped in such a way that the second part covers at least partly the first part of the previous wrap to provide a further compressive effect over the cushioning layer.

However, in the first wrap of bandaging that encircles the body part once, serving as the starting point for subsequent wraps, the compression bandage has no previous wrap to lay against. Consequently, if both the first part and the second part were to initiate from the same position along its length, an extra piece of useless second part would be hanging. This hanging extra piece could hinder the proper application of the compression bandage at the necessary low position. For instance, if the compression bandage would be applied to the calf, starting from the ankle area, it would be needed to start applying the compression bandage slightly above the ankle for the hanging extra piece to not bother the foot.

Thus, it is of interest to start the second part after the first wrap of bandaging of the first part around the body part. This results in a design where the starting portion has an extension of the first part protruding past the end of the second part.

The compression bandage, as sold, should have an extension longer than the circumference of the body part such that the extension can be trimmed to the right size to encircle the body part in a customized manner.

Advantageously, the length of the central portion is at least 70%, preferably at least 80%, preferably at least 90%, of the length of the whole compression bandage. In particular, the central portion is longer than 50 cm, preferably longer than 70 cm, preferably longer than 90 cm.

In a preferred embodiment, in the starting portion and in the central portion, the first part comprises a cushioning material. Given that the compression bandage offers both cushioning and compression within a single layer, the time required for application is significantly reduced.

In particular, in the starting portion and in the central portion, the first part consists only of the cushioning material.

Alternatively, in the starting portion and in the central portion, the first part comprises at least a layer of the cushioning material. This layer extends over the whole length of the first part. In particular, the lay-er of the cushioning material extends over at least the half of the thickness of the first part.

In particular, in the starting portion and in the central portion, the cushioning material extends over the whole width of the first part.

In a preferred embodiment, the cushioning mate-rial is open or closed cell foam, laminated open or closed cell foam, non-woven cushioning or woven cushioning preferably open cell foam or laminated open cell foam, preferably laminated open cell foam.

Open cell foam and laminated open cell foam are advantageous, as they enable a good air flow, moisture and vapor transmission from the patient body through the compression bandage.

The laminate layer present on the upper surface and in particular present on the upper surface of the first part, can be any material known in the art suitable for bandaging a body part including natural and synthetic fibers. Examples could include 100% cotton highly twisted yarns and synthetic fibers including elastane yarns to pro-vide stretch. In a preferred embodiment, the laminate layer present on the upper surface of the first part is a hook receptive nylon/elastane loop fabric suitable for flame lamination.

The laminate layer present on the lower surface and in particular, present on the lower surface of the first part, may be any material known in the art suitable for contact with the skin, including natural and synthetic fibers.

Advantageously, the extension is at least 4%, preferably at least 6%, preferably at least 10% of the length of the compression bandage. In particular, the extension of the first part is longer than 9 cm, preferably longer than 12 cm, preferably longer than 15 cm. Such a length corresponds at least to one circumference of the body part to be wrapped.

In a preferred embodiment, the length of the compression bandage is at least six times, preferably at least eight times, preferably at least ten times, greater than the width of the compression bandage. In particular, the length of the compression bandage is greater than 60 cm, preferably greater than 80 cm, preferably greater than 100 cm.

In particular, at any point along its length, in the starting portion and in the central portion, the second width is at least 60% of the first width, preferably at least equal to the first width. The first width can be between 2 to 8 cm, in particular between 3 to 6 cm, and the second width can be between 2 to 9 cm, in particular between 3 to 7 cm.

Advantageously, at any point along its length, in the starting portion and in the central portion, the first thickness is at least 25% greater, preferably at least 50% greater, preferably at least 100% greater than the second thickness.

In particular, in the starting portion and in the central portion, the first thickness is between 3 to 10 mm, in particular between 5 to 7 mm, and/or the second thickness is between 1 to 5 mm, in particular between 2 mm to 3 mm.

In a preferred embodiment, in the starting portion and in the central portion, the first width is essentially constant, and/or the second width is essentially constant. In particular, in the starting portion and in the central portion, the first thickness is essentially constant and/or the second thickness is essentially constant.

An "essentially" constant thickness means that the thickness of the first part and of the second part are mostly constant and it is not excluded that the thickness is locally different, e.g., due to locally arranged tabs of loop-material and due to manufacturing tolerances. In particular, at least 80%, in particular at least 90% of the first part and/or of the second part have a constant thickness.

In the same way, an "essentially" constant width means that the width of the first part and of the second part are mostly constant and it is not excluded that the width is locally different, e.g., due to manufacturing tolerances. In particular, at least 80%, in particular at least 90% of the first part and/or of the second part have a constant width.

Advantageously, in the starting portion and in the central portion, the first part extends across a part of the width of the compression bandage and the second part extends across the remaining part of the width of the compression bandage.

In particular, in the starting portion and in the central portion, the first part and the second part consist of a first single continuous piece and a second single continuous piece. The first single continuous piece and the second single continuous piece are distinct. The first single continuous piece and the second single continuous piece are distinct in the sense that they do not have joins, seams, or separate parts. They are made of one bloc without any additional pieces attached or assembled. Each single continuous piece may be made of one or multiple materials (e.g. in foam laminate).

In particular, the first part consists of the first single continuous piece and the second part consists of the second single continuous piece.

The first single continuous piece is preferentially open or closed cell foam, laminated open or closed cell foam, non-woven cushioning or woven cushioning, preferably open cell foam or laminated open cell foam, preferably laminated open cell foam.

The laminated open cell foam of the first single continuous piece may have a density of 1 to 10 lb./ft$^3$, which corresponds to a density of 16 to 160 kg/m3.

Preferentially, the second single continuous piece may also be laminated open cell foam, in particular in a compressed form. The laminated open cell foam or the laminated compressed open cell foam of the second single continuous piece may have a density of 3 to 12 lb./ft$^3$, which corresponds to a density of 48 to 192 kg/m3.

Another aspect is the modulus of elasticity of the two materials. The modulus of elasticity of the material of the first single continuous piece may be lower than, equal to, or greater than the modulus of elasticity of the material of the second single continuous piece. In the preferred embodiment, the modulus of elasticity of the material of the first single continuous piece may be lower than the modulus of elasticity of the material of the second single continuous piece.

Advantageously, the first single continuous piece and the second single continuous piece are attached side by side by sewing, in particular by zig-zag stitches bar tacked in at least one location to prevent the stitches from unraveling so that the length of the compression bandage may be cut to length in at least one location. Alternatively, the two pieces can be ultrasonically welded or otherwise secured by tape, adhesives, or any other suitable means.

Advantageously, the compression bandage comprises means for interconnecting different parts of the compression garment. In particular, the means interconnect the lower surface of the second part with the upper surface of the first part. The means may be hook-and-loop fasteners. In particular, the upper surface of the first part may have over its whole surface loop-material and the lower surface of the second part may have tabs of hook-material periodically sewn. The lower surface of the compression bandage corresponds to the surface facing the skin when wrapped around the body part and the upper surface corresponds to the opposite surface, not facing the body part.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein:

FIG. 1*a* shows a compression bandage with an arched shape according to the invention;

FIG. 1*b* shows a compression bandage with a straight shape according to the invention;

FIG. 2*a* shows a sectional view of a first embodiment of the compression bandage;

FIG. 2*b* shows a sectional view of a second embodiment of the compression bandage;

FIG. 2*c* shows a sectional view of a third embodiment of the compression bandage;

MODES FOR CARRYING OUT THE INVENTION

Figure 3A:
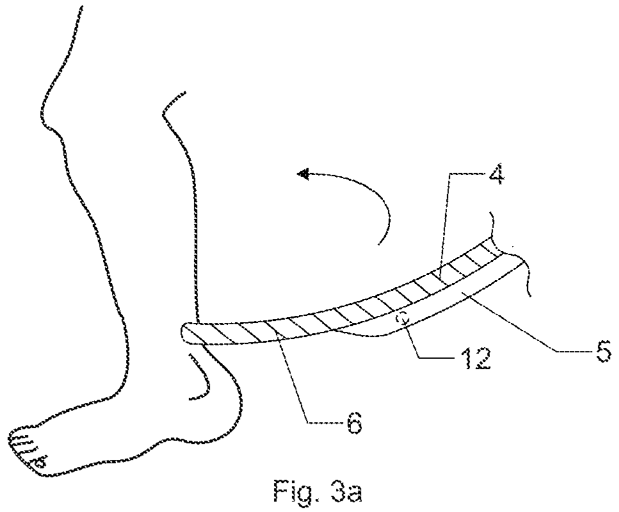
FIGS. 3*a*, 3*b*, 3*c*, and 3*d* show the wrapping of the compression bandage around the calf.
Figure 3B:
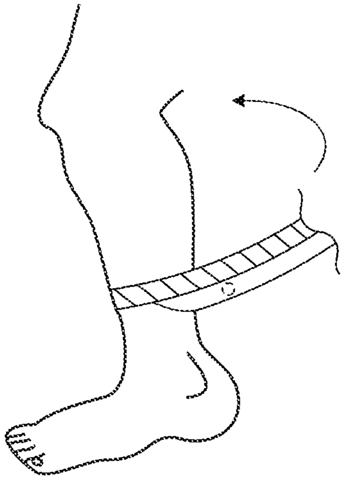
Figure 3C:
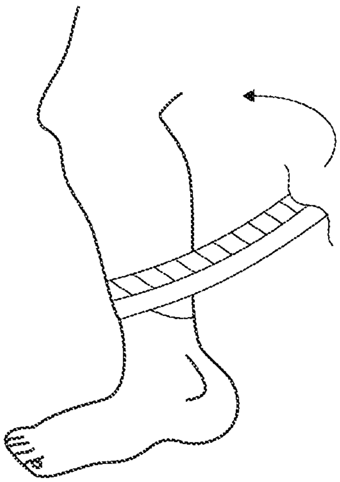
Figure 3D:
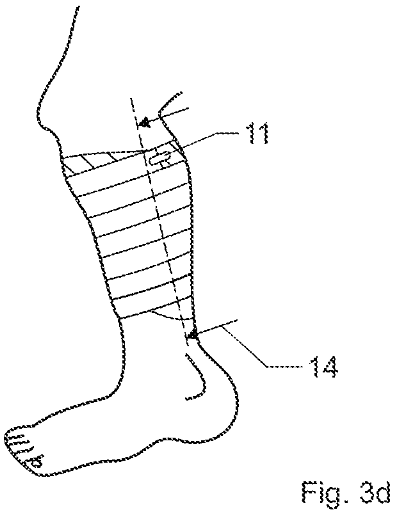

FIG. 1*a* shows a compression bandage with an arched shape according to the invention. The compression bandage is adapted to be wrapped around a body part, in particular a calf, a foot, a thigh or an arm. The compression bandage has a length L and a width W.

The compression bandage consists of a starting portion 1, a central portion 2 and a terminal portion 3. For illustration purposes, these three portions are separated by dashed lines, drawn perpendicular to the longitudinal axis. The central portion 2 is arranged between the starting portion 1 and the terminal portion 3. I.e., the central portion 2 is adjacent to the starting portion 1 and the central portion 2 is adjacent to the terminal portion 3.

The compression bandage consists of two parts. The first part 4 is depicted with a striped pattern. The second part 5 is depicted without any pattern. The starting portion 1, the central portion 2 and the terminal portion 3 comprise a first part 4 and a second part 5. The first part 4 comprises an extension 6 protruding past the end of the second part 5. I.e., the first part 4 extends over the whole length L of the compression bandage while the second part 5 is shorter. The extension 6 is arranged in the starting portion 1.

In the exemplary embodiment, the length of the extension 6 is 35 cm. The extension 6 is longer than the circumference of the body part to be wrapped such that it can be trimmed to the right size.

The first part 4 has the same width as the second part 5. Both, the first part 4 and the second part 5 of the compression bandage, as sold, have square ends. It is recommended for the therapist to trim the ends of the first part 4 and of the second part 5 with scissors as illustrated by the dashed lines. The cutting lines are referenced with numbers, 7*a*, 7*b*, 7*c*. Advantageously, the strips of the first part 4 and of the second part 5 consist of materials that do not fray after being cut.

FIG. 1*b* shows a similar compression bandage. In comparison to FIG. 1*b*, the compression bandage does not have an arched shape. It has a straight shape.

FIG. 2*a* shows a sectional view of the compression bandage at the position 8 in FIG. 1*a*, according to a first embodiment. FIG. 2*b* and FIG. 2*c* show the same sectional view as FIG. 2*a*, but illustrating alternative embodiments. In all three embodiments, shown in FIGS. 2*a* to 2*c*, the first part 4 has a thickness T1, a width W1, and the second part 5 has a thickness T2 and a width W2. The width W1 of the first part 4 and the width W2 of the second part 5 are identical, i.e., both, the first part 4 and the second part 5 each extend over 50% of the width W of the compression bandage, collectively encompassing the whole width W. In an exemplary embodiment, the thickness T1 is 5 mm, the thickness T2 is 2.5 mm, both the widths W1 and W2 are each 4 cm, i.e., the total width Wis 8 cm. The length L of the compression bandage can be 5 meters.

The compression bandage has a lower surface 10 facing the skin when wrapped around the body part and an opposite upper surface 9, not facing the body part. The upper surface 9 is flat. The lower surface 10 is not flat since the thickness of the compression bandage decreases from T1 to T2 in the middle of the width W of the compression bandage.

The embodiment according to FIG. 2*a* consists of only one single continuous piece P1. The first part 4 and the second part 5 are made from the same single continuous piece P1.

Alternatively, as shown in FIG. 2*b*. the compression bandage consists of two single continuous pieces that have been layered. The second single continuous piece P2 extends over the width W of the compression bandage and has a constant thickness corresponding to the second thick-ness T2. The first single continuous piece P1 extends over half of the width W of the compression bandage and is placed on the lower surface of the second single continuous piece P2 in such a way that a side of the first single continuous piece P1 aligns with a side of the second single continuous piece P2. The first single continuous piece P1 has a thickness corresponding to the difference between the first thickness T1 and the second thickness T2. As such, the first part 4 consists of a layer of the first single continuous piece P1 and of a layer of the second continuous piece P2 whilst the second part 5 consists only of the second continuous piece P2.

Regarding the third embodiment shown in FIG. 2*c*, the first single continuous piece P1 extends over half of the width W of the compression bandage and has a constant thickness corresponding to the first thickness T1. The second single continuous piece P2 extends over the other half of the width W of the compression bandage and has a constant thickness corresponding to the second thickness T2. As such, the first part 4 consists only of the first single continuous piece P1 and the second part 5 consists only of the second single continuous piece P2. Preferentially, the first single continuous piece P1 and the second single continuous piece P2 are attached side by side by sewing.

In all three embodiments, the first single continuous piece P1 can be made of open cell foam or laminated open cell foam. The second single continuous piece P2 can be made of compressed open cell foam or laminated compressed open cell foam.

FIGS. 3*a* to 3*d* show how the compression bandage is wrapped around a calf. The ends of the compression bandage have already been trimmed with scissors to the desired length and shape. In a first step, as shown in FIG. 3*a*, the starting portion 1 is wrapped around the ankle. The length of the extension 6 after trimming matches the circumference of the ankle.

After having wrapped the extension 6 of the first part 4 around the ankle the second part 5 starts and the width of the compression bandage doubles. In the following wraps, the second part 5 of the compression bandage covers the first part 4.

The wraps are continued until the calf is covered to the knee. The tab of hook-material 11 is arranged on the end of the terminal portion 3 for securing the end of the compression bandage. The upper layer of the first part 4 and the upper layer of the second part 5 are both loop-material. Half of the tab of hook-material 11 can be attached on the upper surface of the terminal portion 3, whilst the other half is attached to the upper surface of the first part 4 of the previous wrap.

Furthermore, other tabs of hook-material 12 are arranged on the lower surface 10 of the second part 5. When wrapping the compression bandage around the body part, the loop-material of the upper surface of the first part 4 connects with the tabs of hook-material 11 of the lower surface of the second part 5. The tabs of hook-material 12 are shown in FIGS. 2*a* to 2*c* and in FIG. 4. The tabs of hook-material 12 are not visible in FIG. 1 and in FIGS. 3*a* to 3*c* (as they are present on the non-visible surface of the compression bandage) but symbolized by dashed circles.

Figure 4:
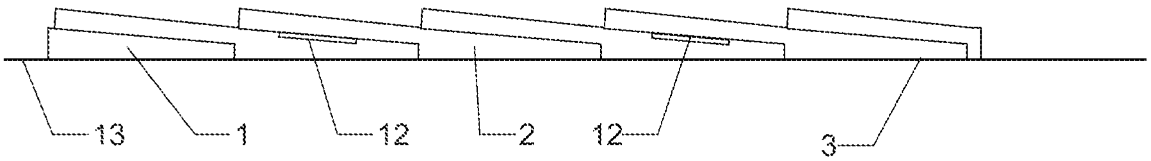
FIG. 4 shows a sectional view of a compression bandage around the calf.

FIG. 4 shows a sectional view of the compression bandage wrapped around the calf. The position of the sectional view is shown by reference number 14 in FIG. 3*d*. The surface of the calf is referenced by number 13. The starting portion 1 is arranged at the ankle. Five more wraps of the central portion 2 follow and at the end of the compression bandage. Tabs of hook-material 12 are arranged at the lower surface of the compression bandage for progressively securing the compression bandage as it is being wrapped around the calf.

The different bandages can be designed for different body parts and for people of different sizes. The dimensions could be as follows:

- for a calf, the width of the bandage can vary from 6 to 12 cm; preferably the bandage has a width of 8 to 10 cm; preferably 8 cm; the length of the bandage can vary from 1.20 to 7.00 m depending on width; For a narrow bandage width of 8 cm, its length can be 1.80 to 5.30 m; for a wide bandage width of 10 cm, its length can be 1.40 to 4.30 m.
- for a foot, the width of the bandage can vary from 4 to 10 cm; preferably the bandage has a width of 6 to 8 cm; preferably 6 cm, the length of the bandage can vary from 0.70 to 5.20 m depending on width; For a narrow bandage width of 6 cm, its length can be 1.20 to 3.50 m; for a wide bandage width of 8 cm, its length can be 0.90 to 2.70 m.
- for a thigh, the width of the bandage can vary from 8 to 14 cm; preferably the bandage has a width of 10 to 12 cm; preferably 12 cm, the length of the bandage can vary from 1.20 to 7.50 m depending on width; For a narrow bandage width of 10 cm its length can be 1.70 to 6.30 m; For a wide bandage width of 12 cm, its length can be 1.50 to 5.30 m.
- for an arm, the width of the bandage can vary from 4 to 10 cm; preferably, the bandage has a width of 6 to 8 cm; preferably 6 cm, the length of the bandage can vary from 1.50 to 10.00 m depending on width; For a narrow bandage width of 6 cm, its length can be 2.40 to 6.70 m; For a wide bandage width of 8 cm, its length can be 1.80 to 5.10 m.
- the bandage may be trimmed at multiple locations to best match the circumference and the length of the limb being wrapped.

The punctual increase in thickness from the second thickness T2 to the first thickness T1 creates a ridge that enables to guide and support each subsequent wrap of the compression bandage. In the embodiment of FIG. 2*c*, in which the first single continuous piece P1 and the second single continuous piece P2 are attached side by side by sewing, the sewn line further provides visual guidance. In this way, it is easy to apply the helicoidal wraps with consistent overlap for both a trained therapist and the patient or home care provider.

The ridge allows each succeeding helicoidal wrap to be mechanically supported by the preceding layer, supporting the compression bandage in place as the body part reduces in size in response to the therapeutic compression applied. Periodically located tabs of hook-material provided on the lower surface of the second part attach to the upper surface of the first part of the pre-ceding layer. In this way, the hook and loop fasteners pro-vide a second means to hold the compression bandage in place even if the body part reduces in circumference.

The tabs of hook-material 12 provide periodic anchoring points to maintain the compression bandage in place whilst, increasing the ease of application for the therapist, the home care provider, or the patient himself.

Due to the ease of application and guidance provided by the ridge of the first part and sewn line to properly locate each compression bandage spiral layer, the compression bandage can easily and reliably be reapplied by the patient or home care provider as the body part circumference reduces in response to the therapeutic compression applied. In this way, proper therapeutic compression can be maintained between clinical sessions.

Thus, the present solution provides a one-piece solution that provides an alternative to the multi-layer bandaging that can be quickly and easily applied by trained professionals, home care providers, and patients.

The invention claimed is:

1. A compression bandage adapted to be wrapped around a body part in a helicoidal manner, wherein the compression bandage has a length (L) and a width (W) and the length (L) is several times greater than the width (W), wherein the compression bandage comprises a starting portion (1) and a central portion (2), wherein the central portion (2) is adjacent to the starting portion (1), the starting portion (1) and the central portion (2) comprise a first part (4) and a second part (5), both extending over the entire length of the central portion (2), the first part (4) extending across a part of the width (W) of the compression bandage and the second part (5) extending across a part of the remaining width of the compression bandage, wherein the first part (4) has a first thickness ($T_1$) and a first width ($W_1$) and the second part (5) has a second thickness ($T_2$) and a second width ($W_2$), wherein at any point along its length, in the starting portion (1) and in the central portion (2), the second width ($W_2$) is at least half the first width ($W_1$) and the first thickness ($T_1$) is greater than the second thickness ($T_2$), characterized in that the starting portion (1) comprises an extension (6) of the first part (4) protruding past the end of the second part (5).

2. The compression bandage according to claim 1, wherein the length of the central portion (2) is at least 70% of the length (L) of the whole compression bandage.

3. The compression bandage according to claim 1, wherein the central portion (2) is longer than 50 cm.

4. The compression bandage according to claim 1, wherein in the starting portion (1) and in the central portion (2), the first part (4) comprises a cushioning material.

5. The compression bandage according to claim 4, wherein in the starting portion (1) and in the central portion (2), the first part (4)

consists of the cushioning material, or comprises at least a layer of the cushioning material extending over the whole length of the first part (4).

6. The compression bandage according to claim 4, wherein the cushioning material extends over the width ($W_1$) of the first part (4).

7. The compression bandage according to claim 4, wherein the cushioning material is open or closed cell foam, laminated open or closed cell foam, non-woven cushioning or woven cushioning.

8. The compression bandage according to claim 1, wherein the extension (6) is at least 4% of the length (L) of the compression bandage.

9. The compression bandage according to claim 1, wherein the extension (6) of the first part (4) is longer than 9 cm.

10. The compression bandage according to claim 1, wherein the length (L) of the compression bandage is at least six times greater than the width (W) of the compression bandage.

11. The compression bandage according to claim 1, wherein the length (L) of the compression bandage is greater than 60 cm.

12. The compression bandage according to claim 1, wherein at any point along its length, in the starting portion (1) and in the central portion (2), the second width ($W_2$) is at least 60% of the first width ($W_1$).

13. The compression bandage according to claim 1, wherein in the starting portion (1) and in the central portion (2), the first width ($W_1$) is between 2 to 8 cm, and the second width ($W_2$) is between 2 to 9 cm.

14. The compression bandage according to claim 1, wherein at any point along its length, in the starting portion (1) and in the central portion (2), the first thickness ($T_1$) is at least 25% greater than the second thickness ($T_2$).

15. The compression bandage according to claim 1, wherein in the starting portion (1) and in the central portion (2), the first thickness ($T_1$) is between 3 to 10 mm, and/or the second thickness ($T_2$) is between 1 to 5 mm.

16. The compression bandage according to claim 1, wherein in the starting portion (1) and in the central portion (2), the first width ($W_1$) is essentially constant, and/or the second width ($W_2$) is essentially constant.

17. The compression bandage according to claim 1, wherein in the starting portion (1) and in the central portion (2), the first thickness ($T_1$) is essentially constant and/or the second thickness ($T_2$) is essentially constant.

18. The compression bandage according to claim 1, wherein in the starting portion (1) and in the central portion (2), the first part (4) extends across a part of the width (W) of the compression bandage and the second part (5) extends across the remaining part of the width (W) of the compression bandage.

19. The compression bandage according to claim 1, wherein in the starting portion (1) and in the central portion (2), the first part (4) and the second part (5) consist of a first single continuous piece ($P_1$) and a second single continuous piece ($P_2$), wherein the first single continuous piece ($P_1$) and the second single continuous piece ($P_2$) are distinct.

20. The compression bandage according to claim 19, wherein the first part (4) consists of the first single continuous piece ($P_1$) and the second part (5) consists of the second single continuous piece ($P_2$).

21. The compression bandage according to claim 20, wherein the first single continuous piece ($P_1$) and the second single continuous piece ($P_2$) are attached side by side by sewing.

* * * * *